United States Patent
Raybin et al.

(10) Patent No.: US 12,349,879 B2
(45) Date of Patent: Jul. 8, 2025

(54) SCOPE-MOUNTED INOD HANDLE

(71) Applicant: Boston Scientific Scimed, Inc., Maple Grove, MN (US)

(72) Inventors: Samuel Raybin, San Jose, CA (US); Michael Powers, Pepperell, MA (US); Gary J. Leanna, Holden, MA (US); Seamus F. O'Shaughnessy, Chelmsford, MA (US); Joseph A. Levendusky, Groton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1308 days.

(21) Appl. No.: 17/029,902

(22) Filed: Sep. 23, 2020

(65) Prior Publication Data

US 2021/0000457 A1    Jan. 7, 2021

Related U.S. Application Data

(63) Continuation of application No. 15/250,478, filed on Aug. 29, 2016, now abandoned.
(Continued)

(51) Int. Cl.
  *A61B 10/04*    (2006.01)
  *A61B 1/00*    (2006.01)
  (Continued)

(52) U.S. Cl.
  CPC .......... *A61B 10/04* (2013.01); *A61B 1/00066* (2013.01); *A61B 1/00128* (2013.01);
  (Continued)

(58) Field of Classification Search
  None
  See application file for complete search history.

(56) References Cited

U.S. PATENT DOCUMENTS

| | | | |
|---|---|---|---|
| 5,599,300 A | 2/1997 | Weaver et al. | |
| 6,514,215 B1* | 2/2003 | Ouchi | A61B 10/04 600/564 |

(Continued)

FOREIGN PATENT DOCUMENTS

| | | |
|---|---|---|
| EP | 1284123 A1 | 2/2003 |
| JP | 2001104315 A | 4/2001 |

(Continued)

*Primary Examiner* — Jay B Shah
(74) *Attorney, Agent, or Firm* — Seager, Tufte & Wickhem, LLP

(57) ABSTRACT

A handle for a medical device includes a distal portion extending longitudinally and including a distal channel extending therethrough, the distal end of the distal portion including a connector configured to connect to a proximal end of an endoscope, a central portion slidably connected to the distal portion, the central portion extending longitudinally. The handle also includes a central channel extending therethrough, the distal end of the central portion connected to a sheath, the central portion including an introducer port extending laterally therefrom so that an auxiliary tool inserted through the introducer port is directed through a lumen of the sheath. Further, the handle includes a proximal portion slidably connected to the central portion, the proximal portion extending longitudinally and including a proximal channel extending therethrough, the distal end of the proximal portion connected to a needle so that the needle is passed through the lumen.

15 Claims, 2 Drawing Sheets

Related U.S. Application Data

(60) Provisional application No. 62/212,866, filed on Sep. 1, 2015.

(51) Int. Cl.
  *A61B 1/018* (2006.01)
  *A61B 8/00* (2006.01)
  *A61B 8/12* (2006.01)
  *A61B 10/02* (2006.01)
  *A61B 17/34* (2006.01)

(52) U.S. Cl.
  CPC ............... *A61B 1/018* (2013.01); *A61B 8/12* (2013.01); *A61B 10/0266* (2013.01); *A61B 10/0283* (2013.01); *A61B 8/445* (2013.01); *A61B 2010/0208* (2013.01); *A61B 2010/045* (2013.01); *A61B 2017/3409* (2013.01); *A61B 2017/3413* (2013.01)

(56) References Cited

U.S. PATENT DOCUMENTS

| | | | |
|---|---|---|---|
| 2012/0078109 A1* | 3/2012 | Okuno | G10K 11/004 600/459 |
| 2013/0104884 A1* | 5/2013 | Vazales | A61M 16/0463 128/202.16 |
| 2013/0226218 A1* | 8/2013 | Binmoeller | A61B 1/018 606/192 |
| 2014/0088456 A1 | 3/2014 | Wang | |

FOREIGN PATENT DOCUMENTS

| | | | | |
|---|---|---|---|---|
| JP | 2002543938 A | 12/2002 | | |
| JP | 2006527603 A | 12/2006 | | |
| WO | WO-2015089372 A1 * | 6/2015 | ......... | A61B 10/0233 |

* cited by examiner

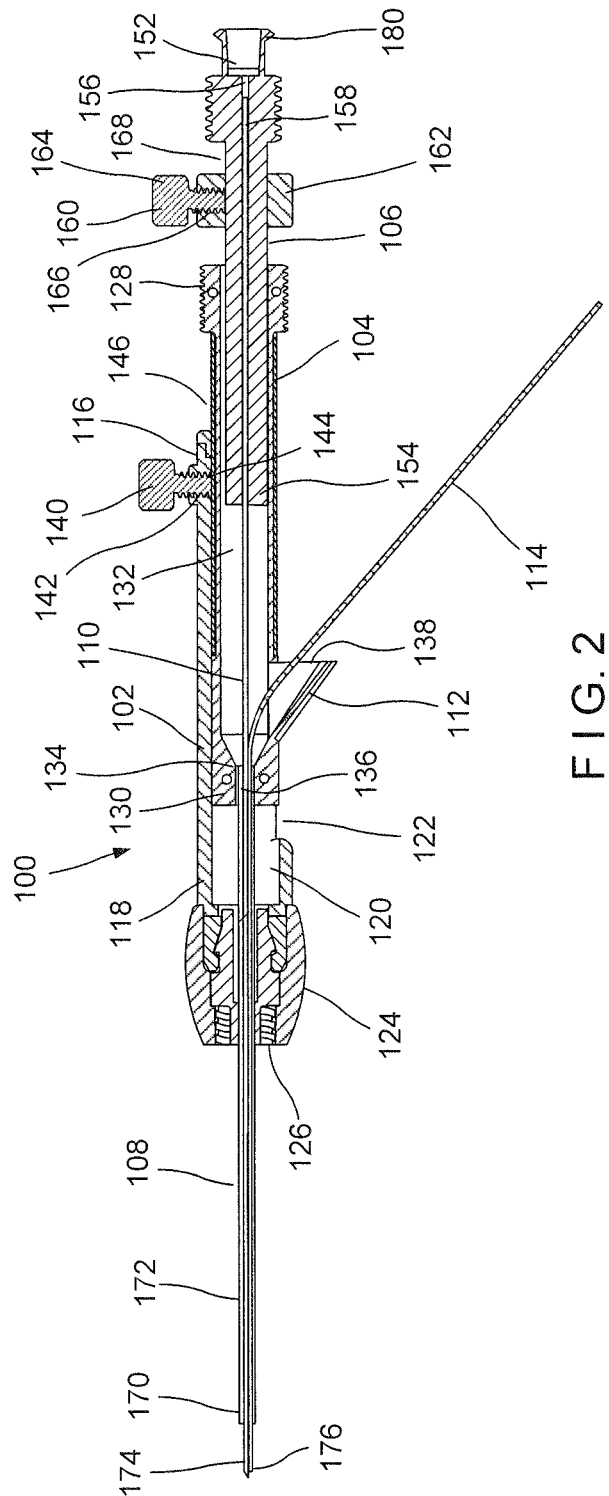
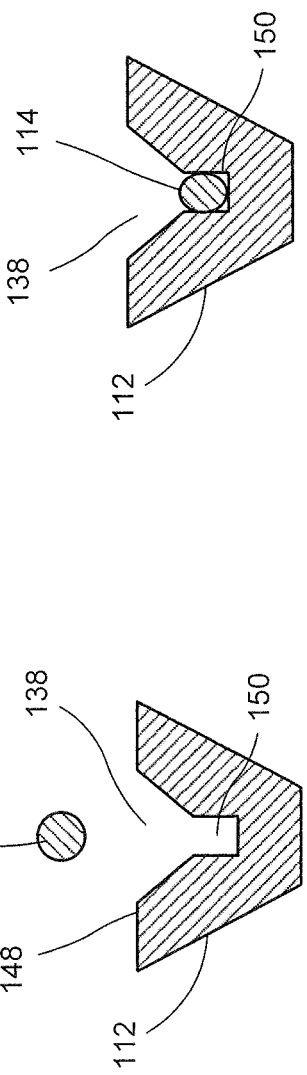
FIG. 2
FIG. 3
FIG. 4

SCOPE-MOUNTED INOD HANDLE

PRIORITY CLAIM

This application is a continuation of Ser. No. 15/250,478, filed Aug. 29, 2016, which claims the benefit of priority under 35 U.S.C. § 119 to U.S. Provisional Application Ser. No. 62/212,866, filed Sep. 1, 2015, the disclosures of which are herein incorporated herein by reference in their entirety.

BACKGROUND

Biopsies may be performed with Endoscopic Ultrasound Fine Needle Aspiration ("EUS-FNA") devices to obtain cells or small samples of tissue from, for example, the breast, liver or lung for cytology studies, endoscopy, oncology or bronchology. As understood by those skilled in the art, biopsy needles enable the capture of samples to facilitate diagnosis and treatment. These biopsy needles are generally connected at their proximal ends to handles to facilitate their insertion into target tissue. Currently available handles are typically formed as two or more overlapping substantially cylindrical elements with a first element attached to an endoscope and a second larger diameter element overlapping a proximal portion of the first element being used to advance the needle into a target site in a living body.

SUMMARY

The present disclosure is directed to a handle for a medical device, comprising a distal portion, a central portion and a proximal portion. The distal portion extending longitudinally from a proximal end to a distal end and including a distal channel extending therethrough, the distal end of the distal portion including a connector configured to connect to a proximal end of an endoscope. The central portion is sized and shaped to be slidably connected to the proximal end of the distal portion, the central portion extending longitudinally from a proximal end to a distal end and including a central channel (i.e., a channel located in the central portion) extending therethrough, the distal end of the central portion being configured to be connected to a sheath, the central portion including an introducer port extending laterally therefrom so that an auxiliary tool inserted through the introducer port is directed through a lumen of the sheath. The proximal portion sized and shaped to be slidably connected to the proximal end of the central portion, the proximal portion extending longitudinally from a proximal end to a distal end and including a proximal channel extending therethrough, the distal end of the proximal portion being configured to be connected to a needle so that the needle is passed through the lumen of the sheath, the distal, central and proximal portions are longitudinally movable relative to one another to adjust a relative positioning between the endoscope, sheath and needle.

In an exemplary embodiment, the distal portion may include a longitudinal slot extending longitudinally from the proximal end thereof, the longitudinal slot sized and shaped to slidably receive the introducer port of the central portion therein.

In an exemplary embodiment, the distal portion may be a C-shaped tube.

In an exemplary embodiment, the proximal end of the proximal portion may include a connection mechanism configured to connect the needle to an aspirating source.

In an exemplary embodiment, the introducer port may include a locking feature for locking the auxiliary tool relative thereto.

In an exemplary embodiment, the locking feature may include one of a slot sized and shaped to wedge a portion of the auxiliary tool therein and a clamp configured to clamp the auxiliary tool to the introducer port.

In an exemplary embodiment, the handle may further comprise a locking element for locking the distal and central portions relative to one another.

In an exemplary embodiment, the locking element may include a thumb screw threadedly engaging a hole extending laterally through the distal portion so that, when in a locked configuration, an end of the thumb screw engages an exterior surface of the central portion.

In an exemplary embodiment, the handle may further comprise an adjustable needle stop configured to limit advancement of the needle relative to the sheath.

In an exemplary embodiment, the adjustable needle stop may include a collar slidably mounted over the proximal portion and a thumb screw threadedly engaging a hole extending laterally through the collar so that, when the thumb screw is tightened within the hole, the adjustable needle stop is fixed in a desired position along the proximal portion, a cross-sectional area of the collar being larger than a cross-sectional area of the central portion.

The present disclosure is also directed to a tissue sampling device, comprising a handle member including a distal portion extending longitudinally from a proximal end to a distal end and including a distal channel extending therethrough, a central portion sized and shaped to be slidably connected to the proximal end of the distal portion, the central portion extending longitudinally from a proximal end to a distal end and including a central channel (i.e., a channel located in the central portion) extending therethrough along with an introducer port extending laterally therefrom, and a proximal portion sized and shaped to be slidably connected to the proximal end of the central portion, the proximal portion extending longitudinally from a proximal end to a distal end and including a proximal channel extending therethrough. The device also comprises an endoscope connected to the distal portion via a connector at the distal end thereof, a sheath extending longitudinally from a proximal end to a distal end and including a lumen extending therethrough, the proximal end of the sheath connected to a distal end of the central portion, and a needle extending longitudinally from a proximal end to a distal, the proximal end of the needle mounted within the proximal channel so that the needle passes through the lumen of the sheath.

In an exemplary embodiment, the device may further comprise an auxiliary tool sized and shaped to be inserted through the introducer port, the auxiliary tool directed through the lumen of the sheath when inserted through the introducer port.

In an exemplary embodiment, the auxiliary tool may be an ultrasound probe.

In an exemplary embodiment, the distal portion may include a longitudinal slot extending longitudinally from the proximal end thereof, the longitudinal slot sized and shaped to slidably receive the introducer port of the central portion therein.

In an exemplary embodiment, the introducer port may include a slot sized and shaped to wedge a portion of the auxiliary tool therein to lock the auxiliary tool relative thereto.

The present disclosure is also directed to a method for tissue sampling, comprising connecting an endoscope to a distal end of a distal portion of a handle member via a connector at the distal end of the distal portion, the handle member including the distal portion, a central portion and a proximal portion slidable with respect to one another, a distal end of the central portion connected to a sheath, which passes through the endoscope, and the proximal portion connected to a needle so that the needle passes through a lumen of the sheath, adjusting the distal portion, the central portion and proximal portion relative to one another so that the endoscope, sheath and needle are in a desired insertion configuration relative to one another, inserting the endoscope to a target area within a living body, advancing the sheath distally out of the endoscope such that a distal end thereof is proximate a target tissue to be sampled, inserting an auxiliary tool into the introducer port and through the sheath, and advancing the needle distally out of the sheath so that a distal end of the needle is inserted into the target tissue to be sampled.

In an embodiment, the auxiliary tool may be an ultrasound probe providing visualization of the target tissue to be sampled.

In an embodiment, the method may further comprise connecting an aspirating source to a proximal end of the proximal portion to provide aspiration to the needle.

In an embodiment, the method may further comprise locking the auxiliary tool relative to the sheath by wedging the auxiliary tool within a slot along the introducer port.

In an embodiment, the method may further comprise adjusting a needle stop mounted over the proximal portion of the handle member to limit a maximum advancement of the needle relative to the sheath

BRIEF DESCRIPTION

FIG. 2 shows a longitudinal cross-sectional view of the device of FIG. 1;

FIG. 3 shows a lateral cross-sectional view of an introducer port and auxiliary tool of the device of FIG. 1, in a first configuration; and FIG. 4 shows a lateral cross-sectional view of the introducer port and auxiliary tool of the device of FIG. 1, in a second configuration.

DETAILED DESCRIPTION

Figure 1:
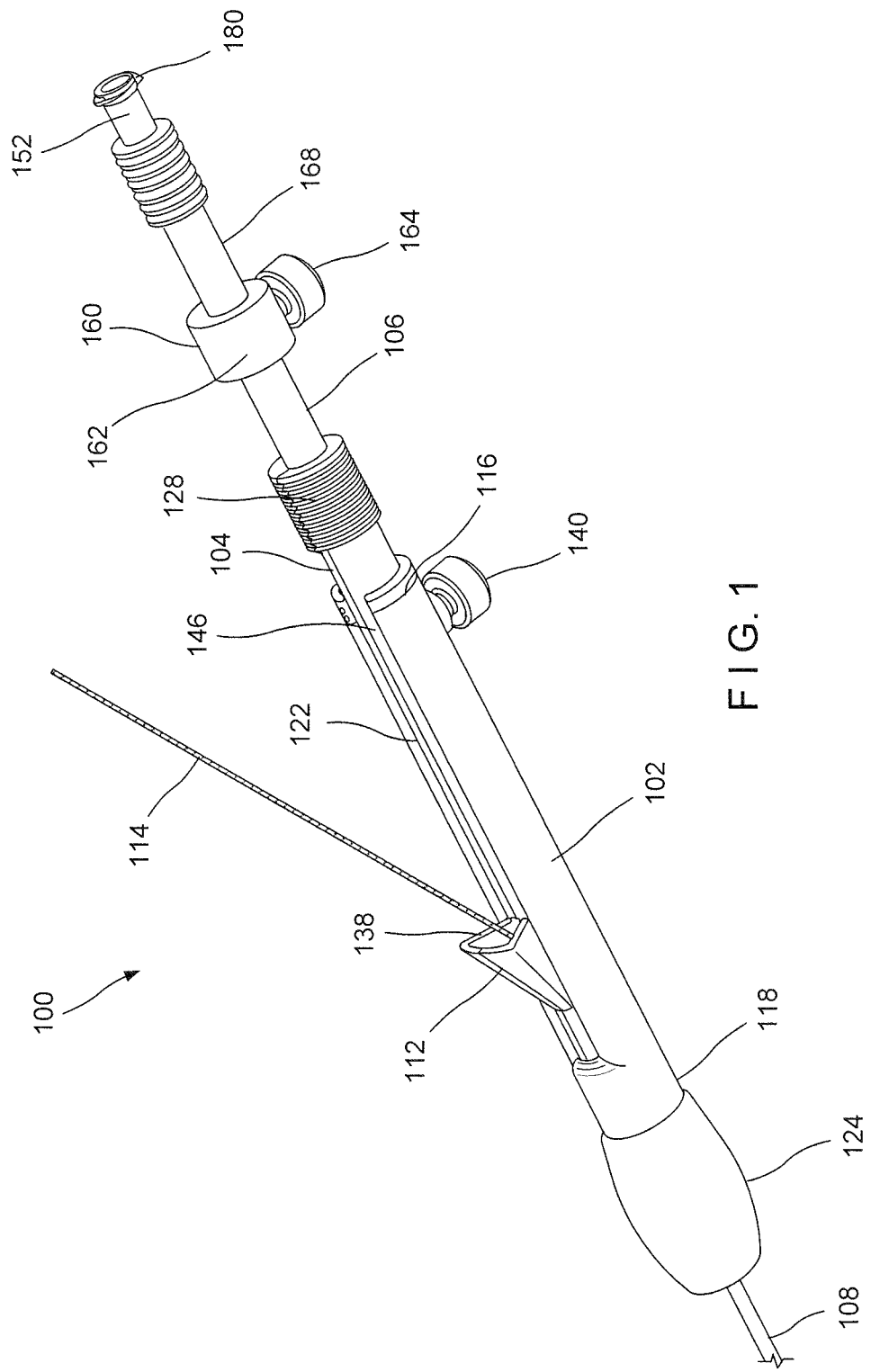
FIG. 1 shows a perspective view of a device according to an exemplary embodiment of the present invention.

The present invention may be further understood with reference to the following description and the appended drawings, wherein like elements are referred to with the same reference numerals. The present invention relates to a handle for an apparatus for obtaining a tissue sample and, in particular, relates to FNA devices. Exemplary embodiments of the handle permit relative movement between a needle and an endoscope through which it is inserted, while also permitting insertion of an auxiliary tool such as, for example, an ultrasound probe. Although the exemplary embodiments specifically describe use of the device during a bronchoscopic procedure, the device of the present invention may be used for any of a variety of endoscopic procedures. It should be noted that the terms "distal" and "proximal," as used herein, are intended to refer to a direction away from (distal) and toward (proximal) a user of the device.

As shown in FIGS. 1-4, a handle device 100 according to an exemplary embodiment of the present invention comprises a distal portion 102, a central portion 104 and a proximal portion 106 slidably coupled to one another in a telescoping fashion so that a sheath 108 and a needle 110 coupled thereto may be moved relative to one another and relative to an endoscope (not shown) to which the handle is coupled via movement of the distal portion 102, central portion 104 and proximal portion 106 relative to one another. The central portion 104 additionally includes an introducer port 112 extending laterally therefrom, through which an auxiliary tool such as, for example, a narrow radial ultrasound probe 114 may be inserted through the sheath 108 alongside the needle 110 to visualize sampling of target tissue via the needle 110. For example, during a bronchoscopic biopsy, the endoscope is inserted through a trachea of the patient to a target area within the lungs. In some cases, however, target tissue to be sampled may be located within secondary or tertiary bronchial passageways, through which the endoscope cannot be inserted. In these cases, the sheath 108 and the needle 110 may be moved distally out of the distal end of the endoscope to enter the secondary and/or tertiary passageways. In such situations, it may not be possible to visualize the actual sampling of the target tissue via the endoscope vision system. As the introducer port 112 permits insertion of the ultrasound probe 114, which is sized to be inserted through even narrow passageways of the body, through the sheath 108 alongside the needle 110, the ultrasound probe 114 may be used to visualize the sampling. This helps ensure that a proper sample of tissue has been obtained by the needle 110 from the target tissue mass.

In particular, the distal portion 102 extends longitudinally from a proximal end 116 to a distal end 118 and includes a distal channel 120 extending therethrough. The distal portion 102 also includes a longitudinal slot 122 extending from the proximal end 116 along a portion of a length thereof. In one embodiment, the distal portion 102 may be configured as a C-shaped tube. The distal end 118 includes a connector 124 configured to be connected to an endoscope. In one embodiment, the connector 124 may be rotatably mounted over the distal end 118 and include an internal threading 126 therein so that the connector 124 may receive a proximal end of the endoscope therein and be rotated relative thereto to threadedly engage the endoscope. In another embodiment, the connector 124 may be non-movably mounted to the distal portion 102 so that the entire distal portion 102 must be rotated relative to the endoscope to threadedly engage the endoscope thereto. Other engagement mechanisms between the endoscope and the connector 124 are also possible. For example, in another embodiment, the connector 124 may be configured to permit a luer lock connection with the endoscope.

The central portion 104 extends longitudinally from a proximal end 128 to a distal end 130 and includes a central channel 132 extending therethrough. The central channel 132 is tapered at a distal end 134 to fix a proximal end 136 of the sheath 108 within the distal end 134 so that the sheath 108 extends along, for example, a central axis of the central portion 104. The central portion 104 may be slidably received through the proximal end 116 of the distal portion 102 within the distal channel 120 so that the central portion 104 and the distal portion 102 may be moved longitudinally relative to one another to move the sheath 108 proximally and distally relative to an endoscope to which the distal portion 102 has been coupled.

Proximally of the proximal end 136 of the sheath 108, the central portion 104 includes the introducer port 112 extending laterally therefrom, in communication with the central channel 132. An opening 138 of the introducer port 112 extends toward the proximal end 128 of the central portion 104 so that an auxiliary tool such as the ultrasound probe 114 may be inserted through the opening 138 of the introducer port 112 into the central channel 132 permitting the ultrasound probe 114 to be inserted through the sheath 108. The tapering of the distal end 134 of the central channel 132 directs the ultrasound probe 114 into the sheath 108 as the ultrasound probe 114 is moved distally relative thereto. The central portion 104 is positioned within the distal portion 102 so that the introducer port 112 is longitudinally slidable within the longitudinal slot 122 and the proximal end 128 of the central portion 104 extends proximally of the proximal end 116 of the distal portion 102.

The introducer port 112 may include a locking feature 148 for locking the ultrasound probe 114 relative thereto. In one exemplary embodiment, as shown in FIGS. 3 and 4, the opening 138 of the introducer port 112 may be sized and shaped to include the locking feature 148, which may be configured as a slot 150 sized to engage the ultrasound probe 114 therein via a friction fit. In particular, once the ultrasound probe 114 has been inserted through the sheath 108 as desired, the ultrasound probe 114 may be wedged into the slot 150, as shown in FIG. 4, to lock the ultrasound probe 114 relative thereto. Although the exemplary embodiments show and describe the locking feature 148 as a slotted wedge, other wedge configurations may also be possible. The locking feature 148 may include any of a variety of locking mechanisms. For example, in another embodiment, the locking feature 148 may be configured as a clamp clampable over the ultrasound probe 114.

The central portion 104 may be locked relative to the distal portion 102 via a locking element 140. The locking element 140 may be configured as, for example, a thumb screw threadedly engaging a hole 142 extending laterally through the distal portion 102. The locking element is movable between a locking configuration, in which an end 144 thereof extends into the distal channel 120 to engage an exterior surface 146 of the central portion 104 to lock the central portion 104 relative to the distal portion, and an unlocked configuration, in which the end 144 does not extend into the distal channel 120 so that the central portion 104 is movable relative thereto. The locking element 144 may be rotated within the hole 142 to move the locking element 144 between the locked and unlocked configurations.

The proximal portion 106 extends longitudinally from a proximal end 152 to a distal end 154 and includes a proximal channel 156 extending therethrough. A proximal end 158 of the needle 110 is fixed within the proximal channel 156. The proximal portion 106 is slidably connected to the proximal end 128 of the central portion 104 and may, for example, be received within the central channel 132 so that the needle 110 extends distally from the proximal portion 106 into the sheath 108 and the proximal end 152 of the proximal portion 106 extends proximally of the proximal end 128 of the central portion 104. Thus, longitudinal movement of the proximal portion 106 relative to the central portion 104 moves the needle 110 proximally and distally with respect to the sheath 108. In one embodiment, a length of the proximal portion 106 may be selected so that, even in a distal-most position relative to the central portion 104, the proximal portion 106 does not interfere with the insertion of auxiliary tools through the introducer port 112. In this embodiment, the proximal portion 106 may be rotatable relative to the central portion 104, and thereby the distal portion 102, so that the needle 110 may be rotated relative to the sheath 108 and endoscope 102 through which the needle 110 is inserted, without rotating the entire device 100. In another embodiment, however, the proximal portion 106 may include an elongated slot extending laterally through a distal portion thereof so that, in a distal-most position relative to the central portion 104, the elongated slot is aligned with the introducer port 112 so that the proximal portion 106 does not interfere with the use thereof.

The proximal end 152 of the proximal portion 106 is configured so that, where desired, a stylet may be inserted through the proximal end 152 into the proximal channel 156 so that the stylet may be passed through the needle 110. The proximal end 152 may also include a connection 180 such as, for example, a luer fitting, configured to couple a syringe or other aspirating source to the needle 110.

The proximal portion 106 may also include an adjustable needle stop 160. In one embodiment, the needle stop 160 may include a collar 162 and a thumb screw 164. The collar 162 is slidably mounted over a portion of the proximal portion 106, proximally of the proximal end 128 of the central portion 104. The collar 162 may be moved to a desired position along the proximal portion 106 and fixed in the desired position via the thumb screw 164. In particular, the thumb screw 164 extends through a correspondingly threaded hole 166 extending laterally through the collar 162 to engage an exterior surface 168 of the proximal portion 106, when the collar 162 is in the desired position. This desired position determines a maximum depth of insertion of the needle 110 relative to the sheath 108. For example, when the collar 162 abuts the proximal end 128 of the central portion 104, the proximal portion 106 is prevented from moving any farther distally relative thereto.

As described above, the sheath 108 and the needle 110 may be passed through an endoscope coupled to the distal portion 102 via the connector 124. Each of the proximal, central and distal portions 106, 104, 102 may be moved longitudinally relative to one another to move the needle 110, sheath 108 relative to one another and to the endoscope. The sheath 108 extends longitudinally from the proximal end 136 fixed within the distal end 134 of the central channel 132 to a distal end 170. The sheath 108 includes a lumen 172 extending therethrough, the lumen 172 sized and shaped to slidably accommodate both the needle 110 and an auxiliary tool such as the ultrasound probe 114. In another embodiment, the sheath 108 may be a double lumen sheath, a first lumen configured to receive the needle 110 and a second lumen configured to receive the auxiliary tool. A length of the sheath 108 may be selected so that, when the central portion 104 is moved distally relative to the distal portion 102, the distal end 170 of the sheath 108 extends distally past a distal end of the endoscope.

The needle 110 may be a standard FNA needle extending from the proximal end 158 to a distal end 174 and including a lumen (not shown) extending therethrough. A length of the needle 110 may be selected so that, when the proximal portion 106 is moved distally with respect to the central portion 104, the distal end 174 of the needle 110 extends distally past the distal end 170 of the sheath 108 to be inserted into the target tissue to be sampled. Similarly, a length of the ultrasound probe 114 may be selected so that, when inserted through the introducer port 112 and into the sheath 108 alongside the needle 110, a distal end 176 of the ultrasound probe 114 is positioned proximate the distal end 174 of the needle 110 to visualize the sampling of the target tissue.

According to an exemplary method using the device 100, an endoscope may be coupled to the device 100 via the connector 124 at the distal end 118 of the distal portion 102. The distal portion 102, central portion 104 and proximal portion 106 may be moved relative to one another to achieve a desired position and/or orientation of the endoscope, sheath 108 and the needle 110 relative to one another. For example, during insertion, the sheath 108 and needle 110 may be positioned so that the distal ends 170, 174, respectively, do not extend distally past the distal end of the endoscope. More particularly, the distal end 174 of the needle 110 also does not extend distally past the distal end 170 of the sheath 108. Once the endoscope, sheath 108 and needle 110 have been positioned relative to one another, as desired, the endoscope, with the sheath 108 and the needle 110 received therein is passed through a body passage until a distal end of the endoscope is proximate a target area within a living body. The endoscope may be inserted through, for example, a bronchial passageway, but may be prevented from passing further into secondary and/or tertiary bronchial passageways. In this case, the sheath 108, with the needle 110 extending therein, is extended distally from the endoscope into the secondary and/or tertiary passageways by moving the central portion 104 distally relative to the distal portion 102.

Once the distal end 170 of the sheath 108 is proximate the target tissue to be sampled, an auxiliary tool such as the ultrasound probe 114 may be inserted into the introducer port 112 and through the lumen 172 of the sheath 108 so that the distal end 176 extends distally past the distal end 170 of the sheath 108 to provide visualization of the tissue to be sampled. Upon positioning the ultrasound probe 114 in a desired position relative to the sheath 108, the ultrasound probe 114 may be fixed in the desired position via the locking feature 148. In one embodiment, the ultrasound probe 114 may be wedged into the slot 150. The needle 110 may then be moved distally relative to the sheath 108 by moving the proximal portion 106 distally relative to the central portion 104 so that the distal end 174 of the needle 110 extends distally past the distal end 170 of the sheath 108. The visualization provided by the ultrasound probe 114 ensures that the target tissue is being correctly sampled via the needle 110.

While embodiments have been described above, a number of modifications and changes may be made without departing from the scope of the disclosure. Thus, it is intended that the present disclosure cover modifications and variations provided that they come within the scope of the appended claims and their equivalents.

The invention claimed is:

1. A tissue sampling device, comprising:
a needle;
a sheath; and
a handle for a medical device, comprising:
a central portion, the central portion comprising a central channel and an introducer port, the central channel extending from a proximal end of the central portion to a distal end of the central portion and being tapered at a distal end of the central channel to fix a proximal end of the sheath within the distal end of the central channel, wherein the introducer port is positioned proximate the proximal end of the central portion, wherein the introducer port is configured to receive an ultrasound probe and direct the ultrasound probe into the central channel and toward the distal end of the central portion; and
a proximal portion, a distal end of the proximal portion slidably connected to the proximal end of the central portion, the proximal portion comprising a proximal channel aligned with the central channel and extending from a proximal end of the proximal portion to the distal end of the proximal portion,
wherein the proximal channel is configured to fix a proximal end of the needle therewithin.

2. The tissue sampling device of claim 1, wherein the proximal end of the proximal portion of the handle comprises a connector that is aligned with the proximal channel.

3. The tissue sampling device of claim 2, wherein the connector is configured to couple an aspirating source to the needle.

4. The tissue sampling device of claim 3, wherein the connector comprises a luer fitting.

5. The tissue sampling device of claim 1, wherein the needle is slidably mounted within the proximal channel.

6. The tissue sampling device of claim 1, wherein the sheath includes a first lumen configured to receive the needle and a second lumen configured to receive the ultrasound probe.

7. The tissue sampling device of claim 1, wherein a junction of the central channel fixes the proximal end of the sheath in alignment with a central axis of the central portion.

8. The tissue sampling device of claim 1, wherein the introducer port includes a locking feature configured to limit movement of the ultrasound probe relative to the introducer port.

9. The tissue sampling device of claim 1, comprising a collar slidably mounted over at least a portion of the proximal portion.

10. The tissue sampling device of claim 9, wherein the collar is configured to limit distal movement of the needle.

11. The tissue sampling device of claim 1, comprising a distal portion with a proximal end and a distal end, the proximal end of the distal portion slidably connected to the distal end of the central portion, and the distal portion comprising a distal channel aligned with the central channel and extending from the proximal end of the distal portion to the distal end of the distal portion.

12. The tissue sampling device of claim 11, comprising a locking element configured to limit movement of the central portion relative to the distal portion.

13. A system, comprising:
a needle;
a sheath;
an ultrasound probe; and
a handle, comprising:
a central portion, the central portion comprising a central channel and an introducer port, the central channel extending from a proximal end of the central portion to a distal end of the central portion and being tapered at a distal end of the central channel to fix a proximal end of the sheath within the distal end of the central channel, wherein the introducer port is positioned proximate the proximal end of the central portion, wherein the ultrasound probe is received by the introducer port and directed into the central channel and towards the distal end of the central portion by the introducer port; and
a proximal portion, a distal end of the proximal portion slidably connected to the proximal end of the central portion, the proximal portion comprising a proximal channel aligned with the central channel and extending from a proximal end of the proximal portion to a distal end of the proximal portion,
wherein the proximal channel is configured to fix a proximal end of the needle therewithin.

14. The system of claim 13, wherein the needle is slidably mounted within the proximal channel.

15. The system of claim 13, wherein a proximal end of a sheath is fixed within the distal end of the central portion, the sheath including a first lumen with the needle disposed therein and a second lumen with the ultrasound probe disposed therein.

\* \* \* \* \*